(12) United States Patent
Dhanoa

(10) Patent No.: US 11,634,428 B2
(45) Date of Patent: Apr. 25, 2023

(54) DEUTERATED ANGIOTENSIN-CONVERTING ENZYME-2 (ACE-2) INHIBITORS

(71) Applicant: Daljit Singh Dhanoa, Del Mar, CA (US)

(72) Inventor: Daljit Singh Dhanoa, Del Mar, CA (US)

( * ) Notice: Subject to any disclaimer, the term of this patent is extended or adjusted under 35 U.S.C. 154(b) by 120 days.

(21) Appl. No.: 17/215,468

(22) Filed: Mar. 29, 2021

(65) Prior Publication Data

US 2022/0306646 A1    Sep. 29, 2022

(51) Int. Cl.
| | |
|---|---|
| C07D 495/04 | (2006.01) |
| C07D 233/64 | (2006.01) |
| A61K 45/06 | (2006.01) |
| C07D 317/60 | (2006.01) |
| A61K 31/4706 | (2006.01) |

(52) U.S. Cl.
CPC ........ C07D 495/04 (2013.01); A61K 31/4706 (2013.01); A61K 45/06 (2013.01); C07D 233/64 (2013.01); C07D 317/60 (2013.01); C07B 2200/05 (2013.01)

(58) Field of Classification Search
None
See application file for complete search history.

(56) References Cited

U.S. PATENT DOCUMENTS

2011/0319461 A1* 12/2011 Partridge ................ A61P 29/00
514/400

* cited by examiner

*Primary Examiner* — Brian J Davis
(74) *Attorney, Agent, or Firm* — Karl Neidert

(57) ABSTRACT

The present invention is concerned with novel deuterated Angiotensin-Converting Enzyme-2 (ACE-2) inhibitors of general structural formula I, their optically active enantiomers and diastereoisomers, and pharmaceutical salts and compositions thereof, as well as combination therapies which include compounds of the present invention, These compounds have high potency and selectivity for Angiotensin-Converting Enzyme-2 (ACE-2) inhibition, and are useful in the treatment of infectious respiratory diseases including the pandemic disease Covid-19, Severe Acute Respiratory Syndrome (SARS-CoV-2), Severe Acute Respiratory Syndrome (SARS-CoV), and other diseases caused by coronaviruses.

10 Claims, No Drawings

DEUTERATED ANGIOTENSIN-CONVERTING ENZYME-2 (ACE-2) INHIBITORS

PRIORITY CLAIM

This application is a continuation-in-part of U.S. Provisional Patent Application No. 63/003,901 which is incorporated by reference in its entirety for all purposes.

SUMMARY OF THE INVENTION

The present invention is concerned with novel deuterated Angiotensin-Converting Enzyme-2 (ACE-2) inhibitors of general structural formula I, their optically active enantiomers and diastereoisomers, and pharmaceutical salts and compositions thereof, as well as combination therapies which include compounds of the present invention,

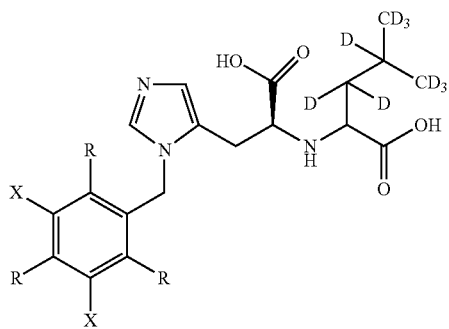

I

Wherein,
R is independently D (Deuterium), H;
X=F, Cl, Br, I, $CD_3$, $CH_3$, $OCD_3$, $OCH_3$.

These compounds have high potency and selectivity for inhibiting Angiotensin-Converting Enzyme-2 (ACE-2), and are useful in the treatment of the pandemic disease Covid-19, Severe Acute Respiratory Syndrome-Coronavirus 2 (SARS-CoV-2), Severe Acute Respiratory Syndrome-Coronavirus (SARS-CoV), and other illnesses caused by various coronaviruses. These ACE-2 inhibitors are also useful for the treatment of cardiovascular, pulmonary, kidney (renal) diseases and other renin-angiotensin-aldosterone system (RAAS) regulated diseases.

The compounds of formula I, their enantiomers, diastereomers, and pharmaceutical salts and combinations thereof, have inhibitory activity for Angiotensin-Converting Enzyme-2 (ACE-2) and are particularly useful for the treatment of the life-threatening pandemic outbreak of the disease Covid-19, Severe Acute Respiratory Syndrome Coronavirus-2 (SARS-CoV-2, Severe Acute Respiratory Syndrome-Coronavirus (SARS-CoV), Middle East Respiratory Syndrome (MERS-CoV), respiratory, pulmonary, cardiovascular, kidney diseases and other renin-angiotensin-aldosterone system (RAAS) regulated diseases.

This invention further constitute a method for inhibiting the enzyme ACE-2 in mammal, including humans, which comprises administering to a mammal in need of such treatment an effective amount of a compound of structural Formula I.

BACKGROUND OF THE INVENTION

Several members of the family Coronaviridae constantly circulate in the human population and usually cause mild respiratory disease (Corman et al., 2019, Internist (Berl.), 2019, 60, 1136-1145). In contrast, the severe acute respiratory syndrome coronavirus (SARS-CoV) and the Middle East respiratory syndrome coronavirus (MERS-CoV) are transmitted from animals to humans and cause severe respiratory diseases in afflicted individuals, SARS and MERS, respectively (Fehr et al., Annu. Rev. Med., 2017, 68, 387-399). SARS emerged in 2002 in Guangdong province, China, and its subsequent global spread was associated with 8,096 cases and 774 deaths (de Wit et al., Nat. Rev. Microbiol., 2016, 14, 523-534). Chinese horseshoe bats serve as natural reservoir hosts for SARS-CoV (Lau et al., Proc. Natl. Acad. Sci. USA, 2005, 102, 14040-14045); Li et al., Science, 2005, 309, 1864-1868). Human transmission was facilitated by intermediate hosts like civet cats and raccoon dogs, which are frequently sold as food sources in Chinese wet markets (Guan et al., Science, 2003, 302, 276-278). At present, no specific antivirals or approved vaccines are available to combat SARS, and the SARS pandemic in 2002 and 2003 was finally stopped by conventional control measures, including travel restrictions and patient isolation.

In December 2019, a new infectious respiratory disease emerged in Wuhan, Hubei province, China (Huang et al., Lancet, China, 2020; Wang et al., Lancet, 2020, 395, 470-473; Zhu et al., N Engl J Med., 2020, 382, 727-733). An initial cluster of infections was linked to Huanan seafood market, potentially due to animal contact. Subsequently, human-to-human transmission occurred (Chan et al., Lancet, 2020, 395, 514-523) and the disease, now termed coronavirus disease 19 (COVID-19) rapidly spread within China and then to South Korea, Iran, Italy, Spain, U.K., USA and virtually the whole world. A novel coronavirus, SARS-coronavirus 2 (SARS-CoV-2), which is closely related to SARS-CoV, was detected in patients and is believed to be the etiologic agent of the new lung disease (Zhu et al., N Engl J Med., 2020, 382, 727-733). On Feb. 12, 2020, a total of 44,730 laboratory-confirmed infections were reported in China, including 8,204 severe cases and 1,114 deaths (WHO, 2020). Infections have spread rapidly due to international travel and continue to increase in numbers throughout the world, particularly China, South Korea, Italy, Spain, Iran, UK, and USA. The total number of Covid-19 patients is rapidly increasing to nearly 1 million cases, with over 48000 deaths. This unprecedented viral disease, Covid-19, has been declared a worldwide pandemic.

The coronavirus COVID-19 pandemic disease has already resulted in more fatalities compared with the SARS (Severe Acute Respiratory Syndrome) and MERS (Middle East Respiratory Syndrome) coronavirus epidemics combined. Therapeutics that may assist to contain its rapid spread and reduce its high mortality rates are urgently needed.

Recently, the crystal structure of the novel coronavirus, SARS-CoV-2 bound to its target receptor on human cells has been reported (Yan et. al., Structural basis for the recognition of SARS-CoV-2 by full-length human ACE2, Science, 2020, 367, 1444-1448). The first step in the entry of the SARS-CoV-2 virus is the binding of the viral trimeric spike protein to the human Angiotensin-Converting Enzyme-2 (ACE2 or ACE-2). This finding offers important insights into the molecular basis for the coronavirus recognition and infection. This important structure provides a basis for the development of novel drugs targeting this crucial binding interaction of the SARS-CoV-2 to the ACE-2.

ACE-2 is expressed in the heart, lungs and kidneys. ACE-2 is a zinc metalloprotease that functions as a carboxypeptidase, While ACE-2 is a carboxypeptidase, the Angiotesin-Converting Enzyme (ACE) is peptidyl-dipeptidase. The catalytic activity of ACE-2 is not suppressed by the known ACE inhibitors, enalapril or lisinopril.

Angiotensin-converting enzyme-2 (ACE-2) is the cellular receptor for severe acute respiratory syndrome-coronavirus (SARS-CoV) and the new (novel) coronavirus (SARS-CoV-2) that has caused the fatal coronavirus disease 2019 (COVID-19) which is ongoing and spreading rapidly and has become a worldwide pandemic at exponential rates since originating in Wuhan China in December 2019. The number of reported Covid-19 patients is approaching one million with over 47000 death worldwide. There are neither any drugs available for treatment nor any vaccines developed for prevention of the disease. Only a few repurposed drugs including the anti-malaria drugs, chloroquine and hydroxychloroquine have been approved this week. A few approved anti-viral drugs are undergoing clinical trials as repurposed drugs for potential treatment of Covid-19 (SARS-CoV-2).

In this invention, we report the design and synthesis of highly potent, selective and novel Angiotensin-Converting Enzyme-2 (ACE-2) inhibitors that show high potential as innovative drugs for the treatment of Covid-19 and other Renin-Angiotensin Aldosterone System (RAAS) regulated diseases including cardiovascular, pulmonary and kidney diseases. These novel ACE-2 inhibitors are discovered by applying our structure-based rational drug design integrated with medicinal chemistry, deuterium chemistry and drug discovery.

DETAILED DESCRIPTION OF THE INVENTION

The present invention is concerned with novel deuterated Angiotensin-Converting Enzyme-2 (ACE-2) inhibitors of general structural formula I, their optically active enantiomers and diastereoisomers, and pharmaceutical salts and compositions thereof, as well as combination therapies which include compounds of the present invention,

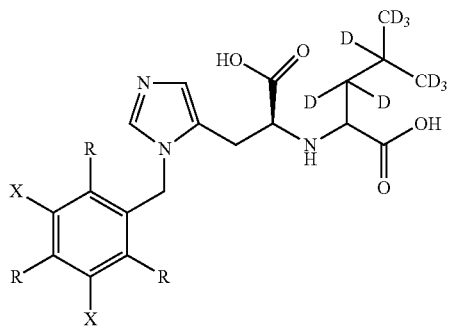

I

Wherein,
R is independently D (Deuterium), H;
X=F, Cl, Br, I, $CD_3$, $CH_3$, $OCD_3$, $OCH_3$.
their optically active or optically pure enantiomers and diastereomers, and pharmaceutically acceptable salts thereof.

These compounds have high potency for inhibiting Angiotensin-Converting Enzyme-2 (ACE-2), and are useful in the treatment of the unprecedented pandemic disease Covid-19 caused by the Severe Acute Respiratory Syndrome-Coronavirus 2 (SARS-CoV-2). The compounds of this invention are also useful for the treatment of Severe Acute Respiratory Syndrome-Coronavirus (SARS-CoV), Middle East Respiratory Syndrome Coronavirus (MERS-CoV), cardiovascular, pulmonary, kidney (renal), liver diseases and other renin-angiotensin-aldosterone system (RAAS) regulated diseases.

The compounds and pharmaceutical compositions of the invention can be used in combination with Chloroquine, Hydroxyquine, angiotensin II receptor (AT1 receptor) antagonists, angiotensin converting enzyme inhibitors, calcium channel antagonists, endothelin receptor antagonists and serotonin subtype receptor 2B (5-$HT_{2B}$) receptor antagonists as well as antiviral compounds and monoclonal antibodies.

Some examples of the angiotensin II receptor antagonists that can be administered in combination of the compounds of this invention (ACE2 inhibitors) includes Losartan, Valsartan, Candesartan, Irbesartan, Olemsartan, Telmisartan and Eprosartan.

The angiotensin converting enzyme (ACE) inhibitors that can be used in combination with compounds of this invention include Enalapril, Lisinopril, Captopril, Benazepril, Fosinopril, Ramipril, Quinapril, and Perindopril.

The calcium channel antagonist that can be used in combination with compounds of this invention include amlodipine, felodipine, Isradipine, Nicardipine, Nifedipine, Nimodipine and Nitrendipine.

The endothelin receptor antagonists that can be used in combination with compounds of this invention include bosentan, macitentan, and an endothelin antagonist, N-(4-isopropyl-$d_7$-benzenesulfonyl)-α-(4-carboxy-2-n-propyl-$d_7$)phenoxy)-3,4-methylenedioxyphenylacetamide, (U.S. patent application No. 62/947,460), shown below.

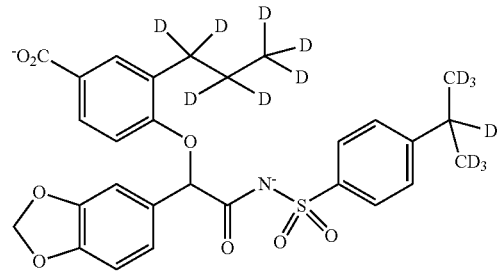

The serotonin (5-HT2B) receptor antagonists that can be used in combination with the compounds of this invention include the 5-$HT_{2B}$ receptor antagonists shown below.

5-((4-((6-chlorothieno[2,3-d]pyrimidin-4-yl-5-d)amino-d)piperidin-1-yl)methyl-d)-2-fluorobenzonitrile (U.S. Pat. No. 8,618,116 B2),

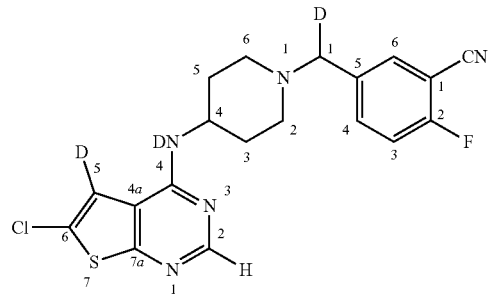

and 5-((4-((6-chlorothieno[2,3-d]pyrimidin-4-yl-2,5-d$_2$) amino-d)piperidin-1-yl)methyl-d$_2$)-2-fluorobenzonitrile (U.S. Pat. No. 8,618,116 B2),

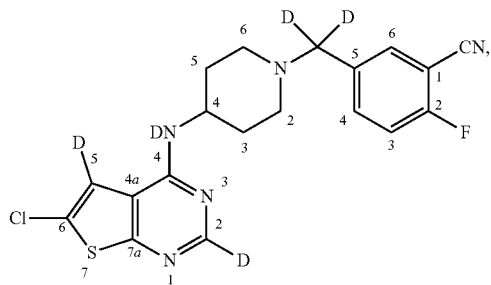

and their pharmaceutically acceptable salts, solvates and enantiomers.

The compounds of the present invention can be used either alone or in combination with other agents described above for the prevention and treatment of Covid-19 and other diseases caused by the viruses (SARS-CoV-2), SARS-CoV, and MERS-CoV. The compounds of this invention can also be used either alone or in combination with other agents described above for the prevention and treatment of t the comorbidities of the pandemic Covid-19 (SARS-CoV-2) including respiratory and lung diseases, pulmonary hypertension, pulmonary fibrosis, cardiovascular, kidney and liver diseases and single and multiple organ failure.

The covid-19 pandemic comorbidities related to pulmonary diseases include pulmonary arterial hypertension, pulmonary hypertension associated with chronic obstructive pulmonary disease (COPD), right ventricular hypertrophy, pulmonary vascular remodeling, lung fibrosis, hypertension, left ventricular hypertrophy, carrhythmia, arterial fibrillation, idiopathic pulmonary fibrosis, idiopathic pulmonary hypertension and asthma.

The covid-19 (SARS-CoV-2) pandemic comorbidities related to cardiovascular diseases include hypertension, congestive heart failure, left ventricular hypertrophy, myocardial infarction, stroke, vasospasm, and Raynaud's disease.

The covid-19 (SARS-CoV-2) pandemic comorbidities related to metabolic diseases include acute kidney disease, chronic kidney disease, renal failure, end-stage renal disease (ESRD), cyclosporin-induced renal failure, Immunoglobulin A nephropathy (IgAN), focal segmental glomerulosclerosis (FSGS), end-stage kidney disease and post-ischemic renal failure, liver fibrosis and liver cirrhosis.

The covid-19 (SARS-CoV-2) pandemic comorbidities also include endotoxic shock, endotoxin- and pathogen induced multiple organ failure, sepsis.

The compounds of this invention can be used alone and in combination with other therapeutic agents for the treatment of Covid-19 (SARS-CoV-2) disease and its comorbidities described above for the prevention and treatment of a mammal in need of treatment of these diseases.

The compounds of this invention, their pharmaceutical compositions that comprise a pharmaceutically effective amount of the compounds and pharmaceutically acceptable carriers of this invention can be used as a monotherapy or a combination therapy with all the therapeutic agents described above for the prevention and treatment of diseases and comorbidities caused by the SARS-CoV-2, SARS-CoV and MERS viruses.

Deuterium (D or $^2$H) is a stable isotope non-radioactive isotope of hydrogen (H) and has an atomic weight of 2.0144. Hydrogen occurs naturally as a mixture of the isotopes $^1$H, D ($^2$H), and T ($^3$H or tritium) and the natural abundance of deuterium is 0-015%. One of ordinary skill in the art recognizes that in all compounds containing H atom, H actually represents a mixture of H and D, with about 0-015% of D. So, compounds with a level of D that has been enriched to be greater than its natural abundance of 0.015%, should be considered unnatural and as a result novel as compared to their corresponding non-enriched counterparts.

The carbon-hydrogen bonds contain a naturally occurring distribution of hydrogen isotopes, namely $^1$H or protium (about 99.9844%), $^2$H or deuterium (D) (about 0.0156%), and $^3$H or tritium (in the range between about 0.5 and 67 tritium atoms per 1018 protium atoms). Higher levels of deuterium incorporation produce a detectable Kinetic Isotope Effect [Werstiuk, N. H.; Dhanoa, D. S.; Timmins, G. Can J. Chem. 1979, 57, 2885; Werstiuk, N. H.; Dhanoa, D. S.; Timmins, G. Can J. Chem. 1983, 61, 2403], that could improve the pharmacokinetic, pharmacologic and/or toxicologic parameters of compounds of formula I in comparison to compounds having naturally occurring levels of deuterium and their corresponding hydrogen (protium) analogs.

Suitable modifications of certain carbon-hydrogen bonds into carbon-deuterium bonds may generate novel substituted compounds of structural formula I with unexpected and non-obvious improvements of pharmacological, pharmacokinetic and toxicological properties in comparison to the non-isotopically enriched compounds. This invention relies on the judicious and successful application of chemical kinetics to drug design. Deuterium incorporation levels in the compounds of the invention are significantly higher than the naturally-occurring levels and are sufficient to induce at least one substantial improvement as described herein. All percentages given for the amount of deuterium present are mole percentages.

"Deuterium enrichment" refers to the percentage of incorporation of deuterium at a given site on the molecule instead of a hydrogen atom. For example, deuterium enrichment of 1% means that in 1% of molecules in a given sample a particular site is occupied by deuterium. Because the naturally occurring distribution of deuterium is about 0.0156%, deuterium enrichment in compounds synthesized using non-enriched starting materials is about 0.0156%.

It can be a significant synthetic challenge to produce 100% deuterium at a specific site of a compound. When 100% deuteration is recited or a deuterium atom is specifically shown in a chemical structure of a compound, a small amount of hydrogen may still be present. Higher levels of deuterium content in a compound can be produced either by Hydrogen-Deuterium (H-D) exchange or by synthesizing the compound for specific deuteration. The H-D exchange is readily achieved in case of H atoms attached to heteroatoms for example in cases of carboxylic acids (COOH), sulfonamides (SO$_2$NH$_2$, CONHSO$_2$-aryl, CONHSO$_2$-alkyl), alcohols (OH), basic amines (NH$_2$), etc. However, these incorporated D attached to heteroatoms (O, N, S) etc, readily revert back to H upon exposure to water or any acidic compounds containing H atoms. The preferred deuterium containing compounds are the ones which contain deuterium directly attached to carbon atoms of the structure of the compounds of this invention.

In some embodiments, the deuterium enrichment in the compounds of the present invention is greater than 4%, 5%, 6%, 7%, 8%, 9% or 10%. In other embodiments, the deuterium enrichment in the compounds of the present invention is greater than 20%. In further embodiments, the deuterium enrichment in the compounds of the present invention is greater than 50%. In some embodiments, the deuterium enrichment in the compounds of the present invention is greater than 70%. In some embodiments, the deuterium enrichment in the compounds of the present invention is greater than 90%.

This invention is concerned with compounds of the general structural formula I, their enantiomers, diastereomers, pharmaceutical acceptable salts and metabolites thereof,

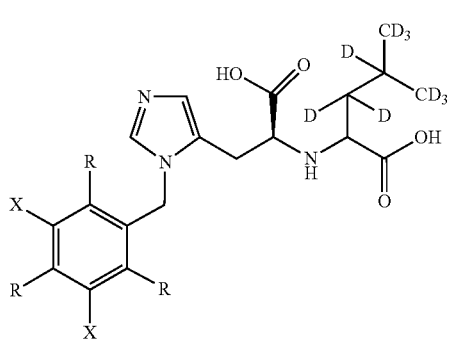

I

Wherein,
R is independently D (Deuterium), H;
X=F, Cl, Br, I, $CD_3$, $CH_3$, $OCD_3$, $OCH_3$.

The reaction scheme conceptualized and used for the synthesis of compounds and intermediates of this invention are general. It will be understood by those skilled in the art of organic synthesis that one or more functional groups present in a given compound of the invention may render the molecule incompatible with a particular synthetic sequence. In such a case an alternative synthetic route, an altered order of steps or a strategy of protection and deprotection may be employed. The reactions are performed in a solvent appropriate to the reagents and materials employed and suitable for the transformation being effected. It is understood by those skilled in the art of organic synthesis that the functionality present on the reactants and reagents being employed should be consistent with the chemical transformations being conducted. Depending upon the reactions and techniques to be used optimal yields may require changing the order of synthetic steps or use of protecting groups followed by deprotection. In all cases the particular reaction conditions, including reagents, solvent, temperature and time, should be chosen so that they are consistent with the nature of the functionality present in the molecule.

The compounds useful in the novel method treatment of this invention form salts with various inorganic and organic acids and bases, which are also within the scope of the invention. Such salts include alkali metal salts like sodium and potassium salts, ammonium salts, alkaline earth metal salts such as calcium and magnesium salts, salts with organic bases for example dicyclohexylamine salts, N-methyl-D-glucamine salts, salts with amino acids e.g., arginine, lysine, etc. In addition, salts with organic and inorganic acids may be prepared, e.g., HCl, HBr, $H_2SO_4$, $H_3PO_4$, methanesulfonic, toluenesulfonic, maleic, fumaric, camphorsulfonic acid.

The salts can be formed by conventional means, such as by reacting the free acid or free base forms of the product with one or more equivalents of the appropriate base or acid in a solvent or medium in which the salt is insoluble, or in a solvent such as water, which is then removed in vacuo or by freeze-drying or by exchanging the cations of an existing salt for another cation on a suitable ion exchange resin.

It will be appreciated that the compounds of general Formula I in this invention may be derivatized at functional groups to provide prodrug derivatives, which are capable of conversion back to the parent compounds in vivo. The concept of prodrug administration has been extensively reviewed (e.g. A. A. Sinkula in Annual Reports in Medicinal Chemistry, Vol 10, R. V. Heinzelmann, E D., Academic Press, New York, London, 1975, Ch 13, pp 306-326; H. Ferres, Drugs of Today, Vol 19, 499-538, 1983, and J. Med. Chem., 18, 172, 1975). Examples of such prodrugs include the physiologically acceptable and metabolically labile ester derivative, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminomethyl esters (e.g. 2-dimethylaminoethyl esters). Additionally, any physiologically acceptable equivalents of the compounds of general structural formula I, similar to the metabolically labile esters, which are capable of producing the parent compounds of general Formula I in vivo, are within the scope of this invention.

It will be further appreciated that the majority of compounds of general Formula I claimed herein are asymmetric and are produced as racemic mixtures of enantiomers and that both the racemic compounds and the resolved individual non-racemic enantiomers are considered to be within the scope of this invention. The compounds of the present invention may have various isomers including all stereoisomers of asymmetric atoms (enantiomers and diastereomers) and geometric, tautomeric or rotamers, and all isomers are considered to be part of the present invention. All processes used to prepare compounds of the present invention and intermediates made therein are considered to be part of the present invention. The racemic compounds of this invention may be resolved to provide individual enantiomers utilizing methods known to those skilled in the art of organic synthesis. For example, diastereoisomeric salts, esters or imides may be prepared from a racemic compound of the Formula I and a suitable optically active amine, amino acid, carboxylic acid, carboxylic ester, alcohol or the like. The diastereoisomeric salts, esters or imides are separated, isolated and purified. The optically active enantiomers are regenerated and the preferred enantiomer is the more potent isomer. The resolved non-racemic chiral enantiomers and diastereoisomers of the compounds of general Formula I, their pharmaceutically acceptable salts and their prodrug forms are also included within the scope of this invention.

"Therapeutically effective amount" includes an amount of a compound of the present invention that is effective when administered alone or in combination to treat the desired condition or disorder. "Therapeutically effective amount" includes an amount of the combination of compounds claimed that is effective to treat the desired condition or disorder. The combination of compounds is preferably a synergistic combination. "Pharmaceutically acceptable salts" refer to derivatives of the disclosed compounds wherein the parent compound is modified by making acid or base salts thereof. Examples of the pharmaceutically acceptable salts include, but not limited to, mineral or organic acid salts of the basic residues. The pharmaceutically acceptable salts include but not limited to HCl, HBr, HI, potassium (K), sodium (Na), calcium (Ca), magnesium (Mg), acetic, trifluoroacetic, citric, ascorbic, benzoin, methanesulfonic (mesylate), benzenesulfonic, bicarbonic, carbonic, ethane disulfonic, edetic, fumaric, maleic, lactic, malic, mandelic, gluconic, glutamic, glycolic, glycollyarsanilic, lauryl, hexylresorcinic, hyrdabamic, hydroxymaleic, hydroxynaphthoic, isethionic, lactobionic, napsylic, nitric, oxalic, pamoic, pantothenic, phenyllacetic, phosphoric, polygalacturonic, propionic, salicyclic, stearic, subacetic, succinic, sulfamic, sulfanilic, sulfuric, tannic, tartaric, tolouenesulfonic, and p-bromobenzenesulfonic.

Synthesis

Preparation of compounds of structural formula I described below are general. It should be understood by those skilled in the art of chemical synthesis that some functional groups may not be compatible for certain synthetic routes and those cases may require appropriate changes including alternative starting materials, building blocks, intermediates, synthesis, synthetic methods process, appropriate sequence of synthetic steps, and compatible protection and deprotection strategy should be employed. The particular reaction conditions, such as reagents, solvents, temperature, and reaction time, should be used for conducting a synthetic reaction consistent with the nature of the functionality of the reactant and products involved.

The synthesis of the ACE-2 inhibitors of Formula I of this invention is illustrated below in Scheme 1. The synthesis begins with the readily available histidine amino acid as its methyl ester 1, which is converted to its Boc-derivative 2 to protect its amino group as described below.

Synthesis of 4-(2-tert-Butoxycarbonylamino-2(S)-methoxycarbonyl-ethyl)-imidazole-1-carboxylic acid tert-butyl ester (Boc-His(Boc)-OMe), 2

Di-tert-butyl dicarbonate ($Boc_2O$, 90 g, 416 mmol, 2 equiv) in methanol (MeOH, 50 mL) is added slowly via an addition funnel to a solution of (S)-histidine methyl ester 1 (50 g, 208 mmol, 1 equiv) in MeOH (500 mL, 0.4 M) and triethylamine (58 mL, 416 mmol, 2 equiv). After 24 hours, the reaction mixture is concentrated completely and the residue was dissolved in dichloromethane (DCM) and water ($H_2O$). The resulting two phases (aqueous and organic) are separated, and the organic phase is washed with brine, dried over $Na_2SO_4$, filtered and concentrated to give a yellow oil, which then is triturated with solvent hexane to yield the di-Boc protected histidine methyl ester 2 as white solid (70 g). $^1$H NMR $CDCl_3$ δ 7.94 (s, 1H), 7.09 (s, 1H), 5.62-5.71 (bm, 1H), 4.50-4.59 (bm, 1H), 3.68 (s, 3H), 2.98-3.04 (bm, 2H), 1.56 (s, 9H), 1.39 (s, 9H). MS: Molecular ion+370.

Synthesis of Methyl N-(t-butoxycarbonyl)-N-(3,5-dichlorobenzyl)-L-histidinate, 4 (R=H, X=Cl)

A solution of 3,5-dicholorobenzyl alcohol, 3 (R=H, X=Cl), (5.3 g, 29.8 mmol, 1.1 equiv) in diisopropylethylamine (DIEA) (5.2 mL, 29.8 mmol, 1.1 equiv) and DCM (25 mL) is added slowly to a cooled solution (−78° C.) of trifluoromethane sulfonic anhydride ($(CF_3SO_2)O$, 5.05 mL, 29.8 mmol, 1.1 equiv) in DCM (100 mL) under argon. After 30 minutes, a solution of the di-Boc protected histidine 2 (10.0 g, 2 mmol, 1 equiv) in DCM (1 M) is added slowly to the in-situ 3,5-dichloro benzyl triflate solution. The reaction mixture is allowed to warm to room temperature overnight. After 24 hours, the reaction mixture is concentrated completely, dissolved in MeOH (150 mL) and heated for 1 hour. The reaction mixture is concentrated and diluted with DCM and EtOAc. The organic phase is washed with saturated aqueous $NaHCO_3$ solution (3 times) and brine (1 time), then dried over anhydrous $Na_2SO_4$, filtered and then concentrated. The resulting oil is purified by column chromotagraphy (gradient 1-10% MeOH in DCM) to give the N-3 alkylated histidine derivative 4 (R=H, X=Cl, 7.5 g,): $^1$HNMR $CDCl_3$ δ7.51 (s, 1H), 7.30 (t, 1H, J=1.8 Hz), 6.94 (s, 2H), 6.88 (s, 1H), 5.16-5.22 (bm, 1H), 5.09 (ABq, 2H, J=16.5 Hz), 4.40-4.48 (m, 1H), 3.74 (s, 3H), 2.89-2.99 (m, 2H), 1.42 (s, 9H). Molecular ion+428, 430.

Synthesis of Methyl (N-(3,5-dichlorobenzyl)-L-histidinate 5 (R=H, X=Cl)

N-Boc-alkylated histidine derivative 4 is treated with 4N HCl in dioxane (100 mL) to remove the Boc protecting group. After 2 hours, the reaction is concentrated and then triturated with ethyl acetate (EtOAc) to give histidine derivative as its di-HCl salt, 5, as a white solid (8.5 g) which is used in the next step.

Carbomethoxy-2-[3-(3,5-dichloro-benzyl)-3H-imidazol-4-yl]-ethylamino}-4-methyl-$d_3$)-pentanoic-benzyl ester-$d_6$,7 (R=H, X=Cl)

To a suspension in dichloroethane (DCE, 200 mL) of the histidine methyl ester derivative 5 (1.0 g, 3.046 mmol) is added deuterated isobutyl keto-ester 6, benzyl 4-(methyl-$d_3$)-2-oxopentanoate-3,3,4,5,5,5-$d_6$, (1.0 g, 4.46 mmol, 1.43 equiv) and the reaction mixture stirred for 1 hour. Sodium triacetoxyborohydride, $NaB(OAc)_3H$ (1.95 g, 9.2 mmol, 3 equiv) is added slowly. After 24 hours, a saturated aqueous $NaHCO_3$ solution is added to the reaction mixture until alkaline and this mixture is stirred further for another 1 hour. The aqueous phase of the reaction mixture is extracted three times with a solvent mixture of dichloromethane (DCM) and ethyl acetate. The combined organic extracts are dried over anhydrous sodium sulfate ($Na_2SO_4$), filtered and concentrated to provide a yellow oil. Purification of the yellow oil using column chromatography (silica gel, ethyl acetate/hexane; ethyl acetate, ethyl acetate/methanol) yields the diester as a 2:1 mixture of diastereomers (0.99 g, 60%): $^1$H NMR $CDCl_3$ δ 7.24-7.50 (m), 6.85-6.94 (m), 5.04-5.14 (m), 3.66 (s), 3.58 (s), 3.27-3.44 (broad m), 3.15-3.21 (broad m), 2.62-2.88 (m), 2.03-2.06 (m), 1.58-1.70 (m), 1.32-1.52 (m), 1.25 (t), 0.77-0.90 (m); Molecular ion+541, 543.

2(S)-{1(S)-Carboxy-2-[3-(3,5-dichloro-benzyl)-3H-imidazol-4-yl]-ethylamino}-4-methyl-$d_3$)-pentanoic acid-$d_6$,8 (R=H, X=Cl)

The diester (0.99 g, 1.9 mmol) is hydrolyzed by stirring a mixture of the diester 7 with 10 mL of an aqueous solution of 1 N NaOH in 10 mL of ethyl alcohol (ethanol) to provide the final product, dicarboxylic acid, 8 as a mixture of diastereomers (40:60). The diastereomers are separated and purified using HPLC and crystallization. The S, S diastereomer: $^1$H NMR MeOD: δ8.58 (s, 1H), 7.47 (bs, 2H), 7.28 (d, 2H, J=1.5 Hz), 5.43 (s, 2H), 3.74 (t, 1H, J=6.9 Hz), 3.63 (t, 1H, J=7.8 Hz), 3.17 (d, 2H, J=6.9 Hz), 1.84-1.98 (m, 1H), 1.61-1.79 (m, 2H), 0.98 (br m, 6H; S, R diastereomer: $^1$H NMR DMSO-d6: δ9.25 (bs, 2H), 7.73 (s, 1H), 7.54 (t, 1H), 7.11 (d, 2H), 6.77 (s, 1H), 5.26 (s, 2H), 3.20 (t, 1H, J=6.1 Hz), 2.98 (t, 1H), 2.59-2.81 (m, 2H), 1.50-1.62 (m, 1H), 1.19-1.35 (m, 2H), 0.78 (br d, 3H), 0.72 (d, 3H). Molecular ion+437, 430. LC-MS Retention time=1.18 min (S, S isomer), 1.35 min (S, R isomer) (gradient 5-100% $CH_3CN$ in $H_2O$, 0.1% formic acid, 4.5 minutes).

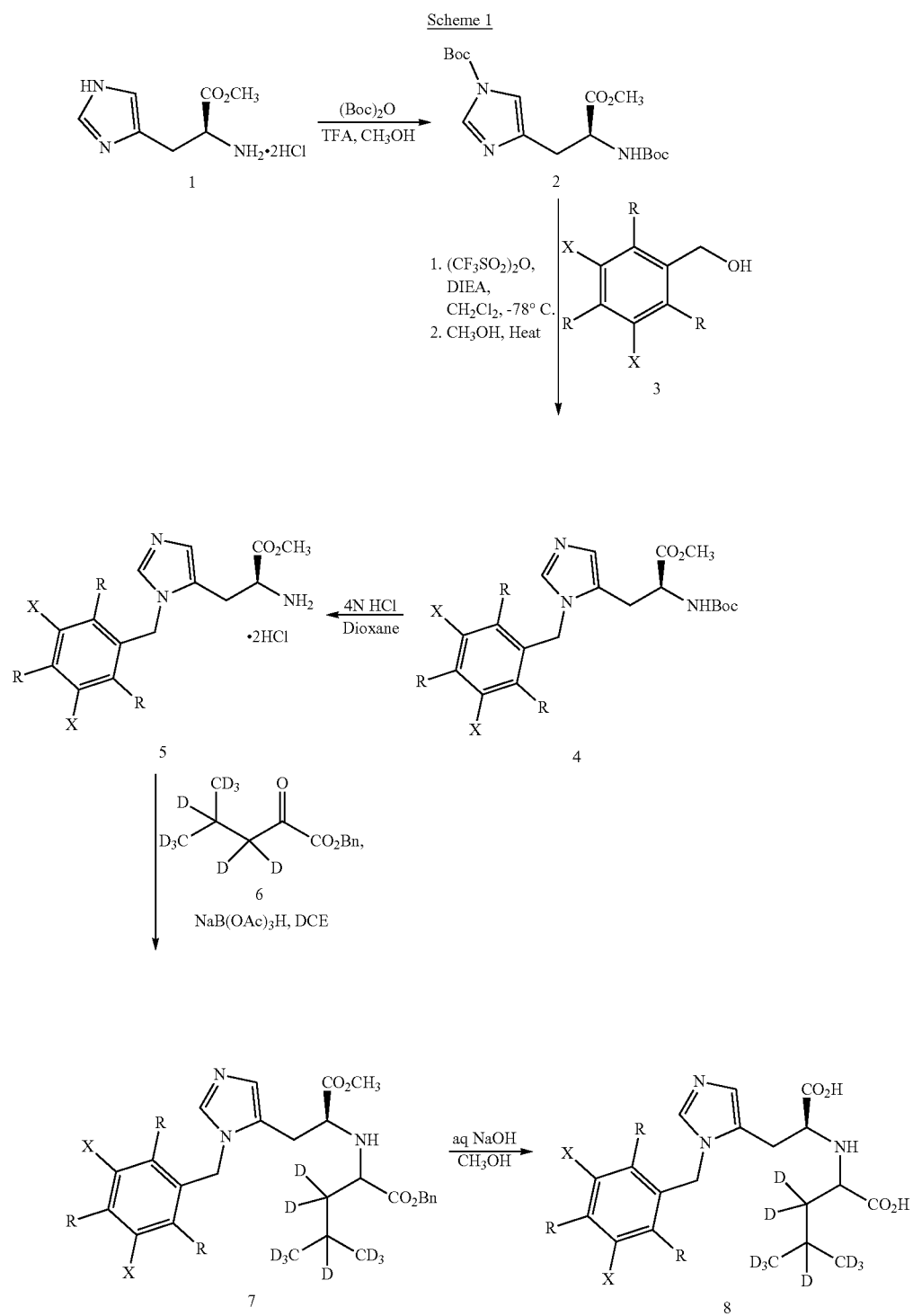

Scheme 1

The final product deuterated compound 8 (as shown in Scheme 1) is also prepared directly from the corresponding undeuterated analog of its precursor 7 using an efficient and extensive deuterium incorporation using a totally catalytic deuterium incorporation by heating a reaction mixture of the substrate with a catalytic (10% by weight of substrate) amount of 10% palladium on carbon in $D_2O$ under hydrogen ($H_2$) atmosphere (in a sealed tube) at 160° C. for 24 hours [Ref. Sajiki, H, et al. Efficient C—H/C-D exchange reaction on the alkyl side chain of aromatic compounds using heterogeneous Pd/C in $D_2O$., Organic Letters (Org. Lett), 2004, 6 (9), 1485-1487], as shown in Scheme 2 below. The deuterated diester derivative obtained by catalytic hydrogenation in $D_2O$ is then hydrolyzed using aqueous solution of NaOH in methanol to yield the target diacid compound 8 shown below in Scheme 2.

Scheme 2

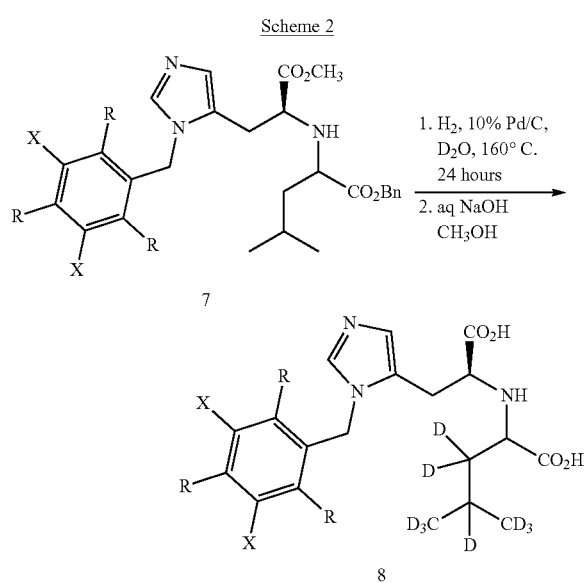

Those skilled in the art will recognize or be able to ascertain using no more than routine experimentation, numerous equivalents to the specific reagents can be utilized to produce compounds of the invention. Numerous modifications and variations of the present invention are possible and therefore it is understood that within the scope of the appended claims, the invention may be practiced otherwise that as specifically described herein. Other aspects, advantages and modifications are within the scope of the invention.

Biological Assays:

Angiotensin-Converting Enzyme-2 (ACE-2 or ACE2) Assay:

Assay for the inhibition of ACE2 is conducted in 384-well microplates at ambient temperature, total volume 50 µL. Compound is added to 50 pM human ACE2 in assay buffer (50 mM MES, 300 mM NaCl, 10 µM ZnCl2, 0.01% Brij-35, pH 6.5). 50 µM MIPH-1 substrate (MCA-Ala-Pro-Lys (DNP)-OH, custom synthesis, Anaspec, Inc., San Diego, Calif.) was added to start the reaction. Activity is monitored by measuring increase in fluorescence (excitation=320 nm, emission=405 nm) over a 60 minute time course using a BMG Polarstar Galaxy fluorescent plate reader (BMG Lab Technologies, Durham, N.C.).

Angiotensin-Converting Enzyme (ACE) Assay:

Assay for the inhibition of ACE is conducted using the same format as ACE2, except compound is added to 1 nM porcine ACE (Sigma-Aldrich Co., St. Louis, Mo.) in assay buffer (50 mM HEPES, 300 mM NaCl, 0.01% Brij-35, pH 7.5) and 50 µM Abz-Gly-p-NO2-Phe-Phe-Pro-OH substrate (Bachem Bioscience, King of Prussia, Pa.) is added to start the reaction.

Carboxypeptidase a (CPDA) Assay:

Assay for the inhibition of carboxypeptidase A (CPDA) is conducted in 96-well microplates at ambient temperature, total volume 300 µL. Compound is added to 500 pM bovine pancreatic CPDA (Sigma-Aldrich Co., St. Louis, Mo.) in assay buffer (50 mM Tris-HCl, 1 M NaCl, pH 7.5). 50 µM FA-Phe-Phe-OH substrate is added to start the reaction. Activity is monitored by measuring decrease in absorbance (328 nm) over a 15 minute time course using a Spectromax 250 absorbance plate reader (Molecular Devices Co., Sunnyvale, Calif.).

Compound $IC_{50}$ values are determined using 10-pt concentration ranges (10 µM-0.005 µM or 100 nM-0.005 nM). Compounds are dissolved in 100% DMSO with the final DMSO concentration in each assay •0.7%. Rates of substrate hydrolysis are determined from time courses and converted to percent (%) inhibition. Percent inhibition is plotted versus compound concentration and fit to the four parameter logistic equation by non-linear regression using Prism Graphpad software (Graphpad Software, Inc., San Diego, Calif.)

Using the methodology described above, representative compounds of this invention are evaluated and found to exhibit $IC_{50}$ values of (<100 nM) thereby demonstrating and confirming the utility of the compounds of this invention as effective ACE-2 Inhibitors.

Accordingly, the novel compounds of the present invention are useful in human therapy for treating the unprecedented fatal pandemic disease Covid-19 caused by SARS-CoV-2. These novel drug candidates also has potential for treating the severe acute respiratory syndrome caused by the virus (SARS-CoV), Middle East Respiratory Syndrome (MERS) and all diseases caused directly or indirectly by or associated with the enzyme Angiotensin-Converting Enzyme 2 (ACE-2) and its receptors and substrates, and renin-angiotensin aldosterone system (also known a serenin-angiotensin system, RAS) by administration to a patient in need of such treatment of a therapeutically effective amount of compounds of this invention and salts thereof.

In the treatment of SARS-CoV-2 (Covid-19), SARS-CoV, the compounds of this invention may be utilized in compositions such as tablets, capsules, injectables or elixirs for oral administration, suppositories for rectal administration, sterile solutions or suspensions for parenteral or intramuscular administration, and the like. The compounds of this invention can be administered to patients (humans and animals) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be appropriately selected which can be administered in single or multiple doses.

The compounds of this invention can also be administered alone and in combination with other drugs including the following drugs, protease inhibitor, Camostat mesylate, anti-malarial drugs including Chloroquine, and hydroxycholoroqine, viral RNA-dependent RNA polymerase drugs including Remdesivir, Ribavirin, Pimodivir, Penciclover, Galidisivir, Favipiravir, and Baloxavir marboxil, and antiviral drug Baricitinib and viral protease inhibitors including Darunavir, Lopinavir, Ritonavir, and viral protein expression drug Nitazoxanide, and viral surface protein drug Umifenovir. and ribonucloside analogs for example EIDD-2801; comprising a therapeutically effective amount of the novel compound of this invention together with a pharmaceutically acceptable carrier therefor.

A compound or mixture of compounds of Formula I or a physiologically acceptable salt is compounded with a physiologically acceptable vehicle, carrier, excipient, binder, preservative, stabilizer, flavor etc., in a unit dosage from as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrytalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is capsule, it may contain, in addition to materials of the above type, a liquid carrier such as fatty oil. Various other materials may be present as coatings or to otherwise modify the physical form of the dosage limit.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

What is claimed is:

1. A deuterium enriched compound of structural formula I,

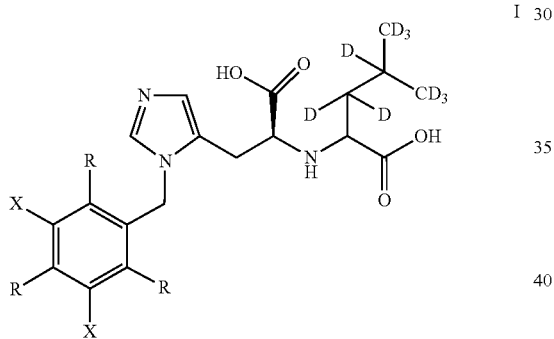

a diastereomer, enantiomer, or a pharmaceutically acceptable salt thereof, wherein, R is independently D (Deuterium), H;

X=F, Cl, Br, I, $CD_3$, $CH_3$, $OCD_3$, $OCH_3$.

2. The deuterium-enriched compounds of claim 1 selected from the group consisting of:

(a) 2(S)-{1(S)-Carboxy-2-[3-(3,5-dichloro-benzyl)-3H-imidazol-4-yl]-ethylamino}-4-(methyl-$d_3$)-pentanoic acid-$d_6$,

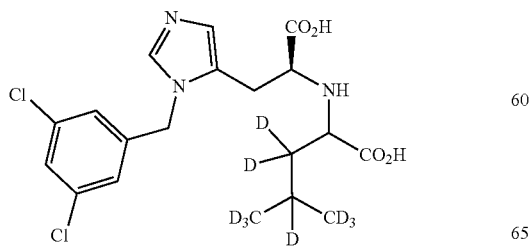

(b) 2(S)-{1(S)-Carboxy-$d_1$-2-[3-(3,5-dichloro-benzyl)-3H-imidazol-4-yl]-ethylamino-$d_1$}-4-(methyl-$d_3$)-pentanoic acid-$d_7$,

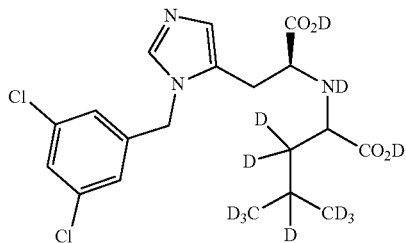

(c) 2(S)-{1(S)-Carboxy-2-[3-(3,5-dichloro-benzyl-$d_2$)-3H-imidazol-4-yl]-ethylamino}-4-(methyl-$d_3$)-pentanoic acid-$d_6$,

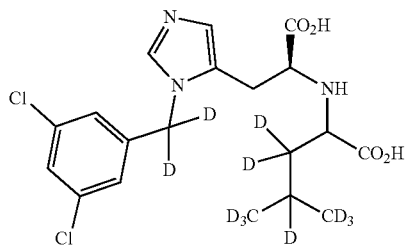 [SMILES: [2H]C([2H])(c1cc(Cl)cc(Cl)c1)n1cncc1C[C@H](NC(C(=O)O)C([2H])([2H])C([2H])(C([2H])([2H])[2H])C([2H])([2H])[2H])C(=O)O]

(d) 2(S)-{1(S)-Carboxy-2-[3-(3,5-dichloro-benzyl-$d_5$)-3H-imidazol-4-yl]-ethylamino}-4-(methyl-$d_3$)-pentanoic acid-$d_6$,

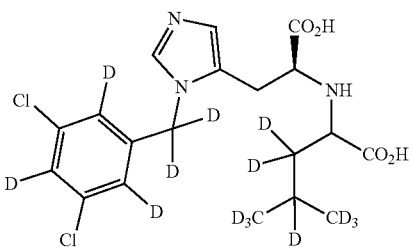 [SMILES: [2H]c1c(Cl)c([2H])c(C([2H])([2H])n2cncc2C[C@H](NC(C(=O)O)C([2H])([2H])C([2H])(C([2H])([2H])[2H])C([2H])([2H])[2H])C(=O)O)c([2H])c1Cl]

(e) 2(S)-{1(S)-Carboxy-2-[3-(3,5-dichloro-benzyl-$d_5$)-3H-imidazol-4-yl]-ethylamino}-4-(methyl-$d_3$)-pentanoic acid-$d_7$,

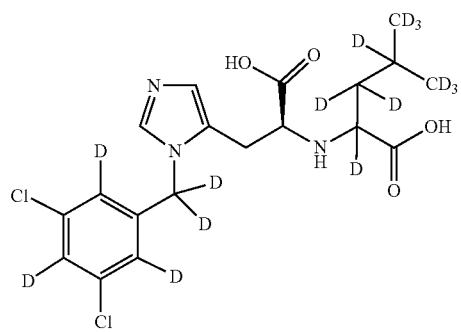 [SMILES: [2H]c1c(Cl)c([2H])c(C([2H])([2H])n2cncc2C[C@H](NC([2H])(C(=O)O)C([2H])([2H])C([2H])(C([2H])([2H])[2H])C([2H])([2H])[2H])C(=O)O)c([2H])c1Cl]

(f) 2(S)-{1(S)-Carboxy-2-[3-(3,5-dichloro-benzyl-d₅)-3H-imidazol-4-yl]-ethylamino-d₂}-4-(methyl-d₃)-pentanoic acid-d₇,

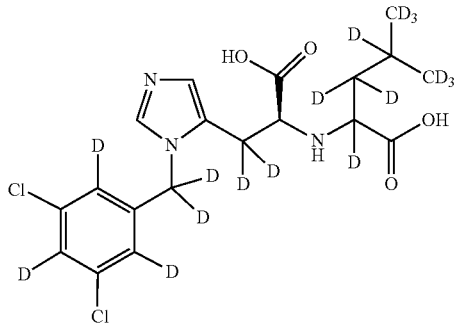 [SMILES: [2H]c1c(Cl)c([2H])c(C([2H])([2H])n2cncc2C([2H])([2H])[C@H](NC([2H])(C(=O)O)C([2H])([2H])C([2H])(C([2H])([2H])[2H])C([2H])([2H])[2H])C(=O)O)c([2H])c1Cl]

(g) 2(S)-{1(S)-Carboxy-2-[3-(3,5-dimethyl-benzyl)-3H-imidazol-4-yl]-ethylamino}-4-(methyl-d₃)-pentanoic acid-d₆,

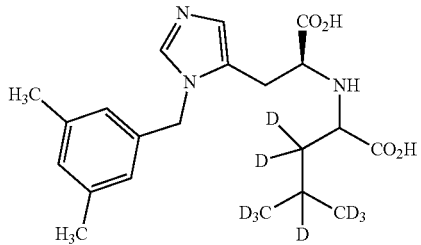

(h) 2(S)-{1(S)-Carboxy-2-[3-(3,5-(dimethyl-d₆)-benzyl)-3H-imidazol-4-yl]-ethylamino}-4-(methyl-d₃)-pentanoic acid-d₆,

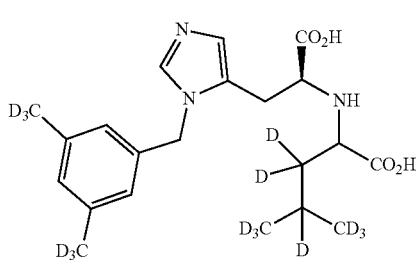 [SMILES: [2H]C([2H])([2H])c1cc(Cn2cncc2C[C@H](NC(C(=O)O)C([2H])([2H])C([2H])(C([2H])([2H])[2H])C([2H])([2H])[2H])C(=O)O)cc(C([2H])([2H])[2H])c1]

(i) 2(S)-{1(S)-Carboxy-d₁-2-[3-(3,5-(dimethyl-d₆)-benzyl)-3H-imidazol-4-yl]-ethylamino-d₁}-4-(methyl-d₃)-pentanoic acid-d₇,

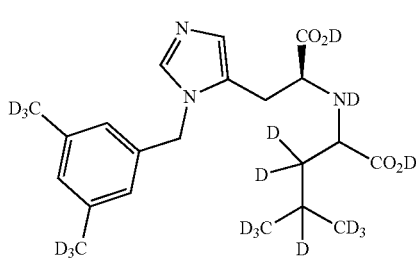

(j) 2(S)-{1(S)-Carboxy-2-[3-(3,5-(dimethyl-d₆)-benzyl)-3H-imidazol-4-yl]-ethylamino}-4-(methyl-d₃)-pentanoic acid-d₇,

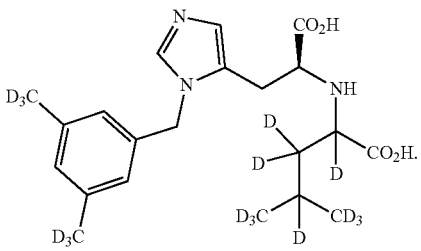 [SMILES: [2H]C([2H])([2H])c1cc(Cn2cncc2C[C@H](NC([2H])(C(=O)O)C([2H])([2H])C([2H])(C([2H])([2H])[2H])C([2H])([2H])[2H])C(=O)O)cc(C([2H])([2H])[2H])c1]

3. A pharmaceutical composition comprising a pharmaceutical vehicle or diluent and one compound of claim 1 in an amount effective for the treatment of a disease selected from Covid-19, SARS-CoV-2, SARS-CoV, and MERS-CoV.

4. A method of treating a disease selected from Covid-19, SAR-CoV-2, SARS-CoV, MERS-CoV comprising administering a pharmaceutically effective amount of the pharmaceutical composition of claim 3.

5. The method of claim 4 wherein the pharmaceutical composition is administered in combination with angiotensin II receptor antagonists, angiotensin converting enzyme inhibitors, calcium channel antagonists, endothelin receptor antagonists, serotonin 5-HT$_{2B}$ receptor antagonists.

6. The method of claim 5, wherein the angiotensin II receptor antagonist is selected from Losartan, Valsartan, Candesartan, Irbesartan, Olemsartan, Telmisartan and Eprosartan.

7. The composition of claim 5, wherein the angiotensin converting enzyme inhibitor is selected from Enalapril, Lisinopril, Captopril, Benazepril, Fosinopril, Ramipril, Quinapril, and Perindopril.

8. The method of claim 5, wherein the calcium channel antagonist is selected from amlodipine, felodipine, Isradipine, Nicardipine, Nifedipine, Nimodipine and Nitrendipine.

9. The method of claim 5, wherein the endothelin receptor antagonist is selected from bosentan, macitentan, and the endothelin antagonist shown as (a) below, (a) N-(4-isopropyl-d₇-benzenesulfonyl)-α-(4-carboxy-2-n-propyl-d₇)phenoxy)-3,4-methylenedioxyphenylacetamide,

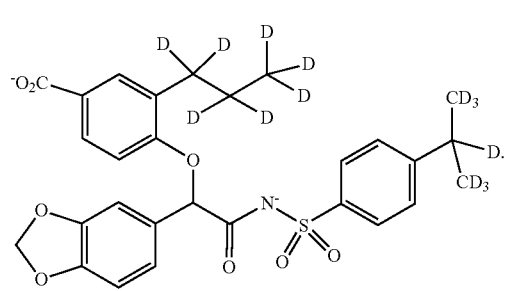

10. The method of claim 5, wherein the serotonin (5-HT2B) receptor antagonist is selected from 5-HT$_{2B}$ receptor antagonists shown below

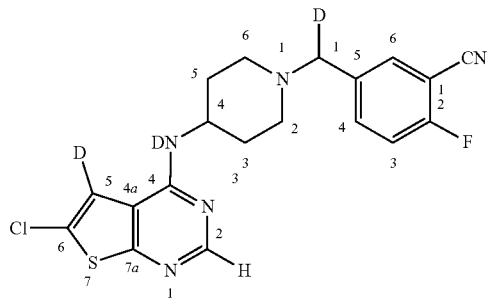

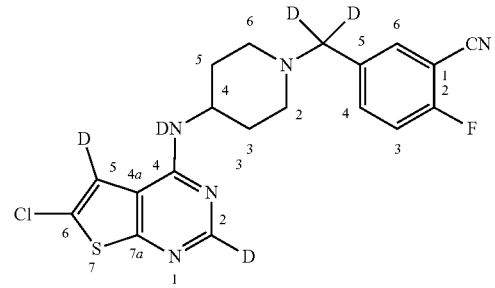

5-((4-((6-chlorothieno[2,3-d]pyrimidin-4-yl-5-d)amino-d)piperidin-1-yl)methyl-d)-2-fluorobenzonitrile, and 5-((4-((6-chlorothieno[2,3-d]pyrimidin-4-yl-2,5-d$_2$)amino-d)piperidin-1-yl)methyl-d$_2$)-2-fluorobenzonitrile, and their pharmaceutically acceptable salts, solvates and enantiomers.

* * * * *